US009839683B2

United States Patent
Locht et al.

(10) Patent No.: US 9,839,683 B2
(45) Date of Patent: *Dec. 12, 2017

(54) VACCINE FOR PROPHYLAXIS OR TREATMENT OF AN ALLERGEN-DRIVEN AIRWAY PATHOLOGY

(71) Applicants: Institut National de la Sante et de la Recherche Medicale (INSERM), Paris (FR); Institut Pasteur de Lille, Lille (FR); National University of Ireland Maynooth, Maynooth (IE)

(72) Inventors: Camille Locht, Brussels (BE); Bernard Mahon, Maynooth (IE); Heather Kavanagh, Dublin (IE)

(73) Assignees: Institut National de la Sante et de la Recherche Medicale, Paris (FR); Institut Pasteur de Lille, Lille (FR); National University of Ireland Maynooth, Maynooth (IE)

(*) Notice: Subject to any disclaimer, the term of this patent is extended or adjusted under 35 U.S.C. 154(b) by 5 days.

This patent is subject to a terminal disclaimer.

(21) Appl. No.: 14/609,461

(22) Filed: Jan. 30, 2015

(65) Prior Publication Data

US 2015/0182614 A1 Jul. 2, 2015

Related U.S. Application Data

(60) Continuation of application No. 13/782,754, filed on Mar. 1, 2013, now Pat. No. 8,986,709, which is a division of application No. 13/266,561, filed as application No. PCT/EP2010/055507 on Apr. 26, 2010, now abandoned.

(30) Foreign Application Priority Data

Apr. 28, 2009 (EP) .................................... 09305371

(51) Int. Cl.
*A61K 39/02* (2006.01)
*A61K 39/00* (2006.01)

(52) U.S. Cl.
CPC ...... *A61K 39/099* (2013.01); *A61K 2039/522* (2013.01); *A61K 2039/523* (2013.01); *A61K 2039/543* (2013.01); *A61K 2039/544* (2013.01)

(58) Field of Classification Search
None
See application file for complete search history.

(56) References Cited

U.S. PATENT DOCUMENTS 6,660,261 B1 12/2003 Mielcarek

OTHER PUBLICATIONS

Kim et al. Immunology 2004 112:624-630.*
Kim, Young-Suk, et al.: "Inhibition of murine allergic airway disease by Bordetella pertussis," Immunology, 2004, vol. 112:624-630.
Grueber, C. et al: "Common vaccine antigens inhibit allergen-induced sensitization and airway hyperresponsiveness in a murine model," Allergy, 2006, vol. 61:820-827.
Zeddeman, A. et al: "Investigations into the emergence of pertactin-deficient Bordetella pertussis isolates in six European countries, 1996 to 2012," Research Articles, Aug. 21, 2014, pp. 1-11; <<www.eurosurveillance.org.>>.
Thorstensson, R. et al: "A Phase I Clinical Study of a Live Attenuated Bordetella pertussis vaccine—BPZE1; A Single Centre, Double-Blind, Placebo-Controlled, Dose-Escalating Study of BPZE1 Given intranasally to healthy adult male volunteers," PLOS ONE, Jan. 2014, vol. 9, No. 1:10.

* cited by examiner

*Primary Examiner* — Oluwatosin Ogunbiyi
(74) *Attorney, Agent, or Firm* — Stanley A. Kim

(57) ABSTRACT

The present invention relates to a live attenuated *Bordetella pertussis* vaccine which is deficient for tracheal cytotoxin (TCT), pertussis toxin (PTX), and dermonecrotic toxin (DNT) for prophylaxis or treatment of an allergen-driven airway pathology.

Figure 1:
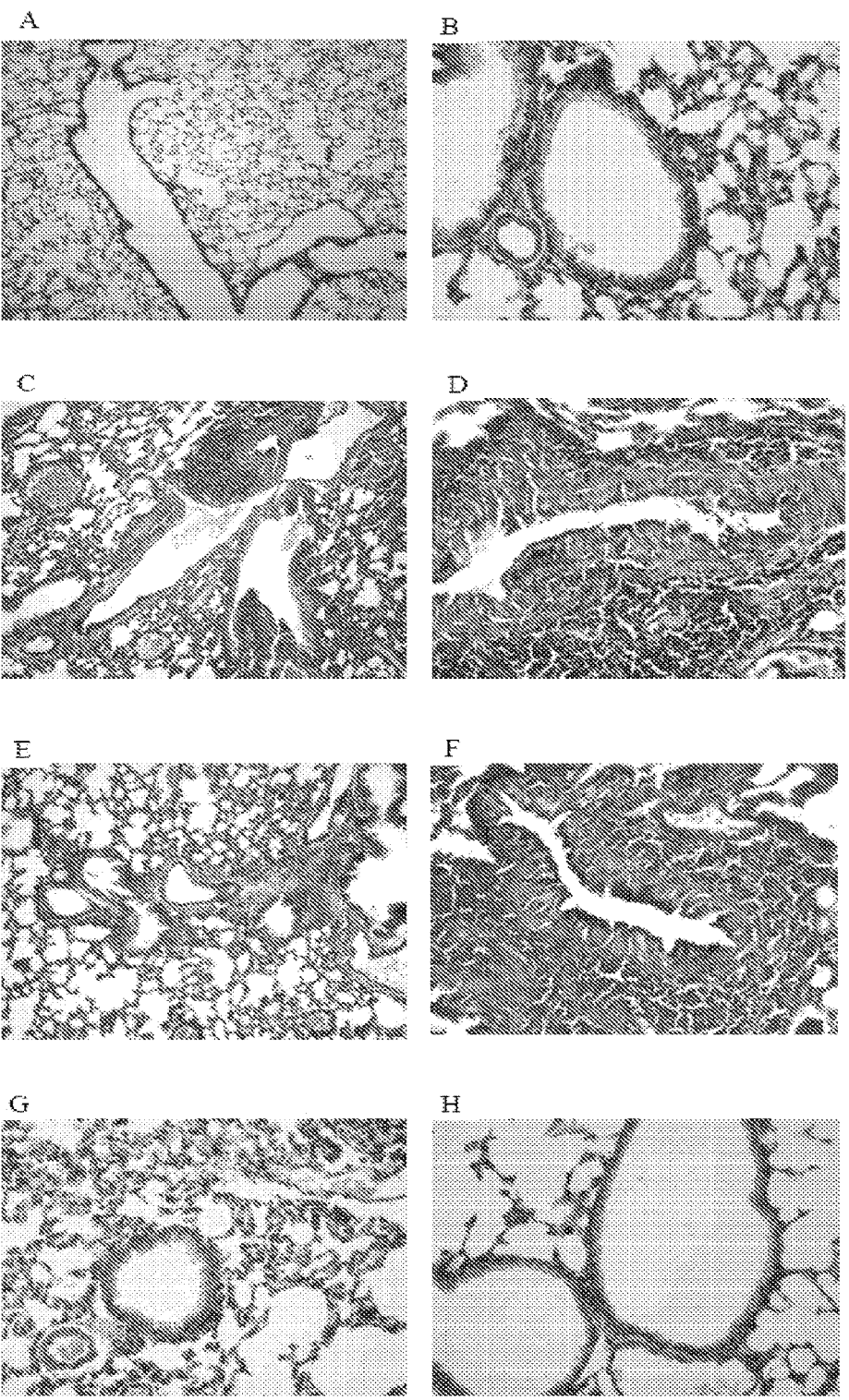

6 Claims, 5 Drawing Sheets

VACCINE FOR PROPHYLAXIS OR TREATMENT OF AN ALLERGEN-DRIVEN AIRWAY PATHOLOGY

CROSS-REFERENCE TO RELATED APPLICATION

This application is a continuation application of U.S. patent application Ser. No. 13/782,754 filed on Mar. 1, 2013, now U.S. Pat. No. 8,986,709 issued on Mar. 24, 2015, which is a divisional application of U.S. patent application Ser. No. 13/266,561, now abandoned, which was filed pursuant to 35 U.S.C. 371 as a U.S. National Phase application of International Patent Application No. PCT/EP2010/055507, which was filed on Apr. 26, 2010, claiming the benefit of priority to European Patent Application No. 09305371.8, which was filed on Apr. 28, 2009. The entire text of the aforementioned applications is incorporated herein by reference in its entirety.

FIELD OF THE INVENTION

The present invention relates to a vaccine for prophylaxis or treatment of an allergen-driven airway pathology.

BACKGROUND OF THE INVENTION

The pathogenesis of allergic asthma remains unclear, however, the current understanding involves the expansion of CD4+Th2 cells, and a breakdown in tolerance to otherwise innocuous environmental allergens (Romagnani et al. J Allergy Clin Immunol 2004; 113(3):395-400). Genetic predisposition, coupled with environmental influences appears to affect the regular suppression of Th2-mediated responses. It has been hypothesized that abnormalities in the maturation of the lung during fetal and neonatal development may render the airways more susceptible to environmental allergens, favoring polarization towards the Th2 phenotype and thus, predisposing the individual to atopy and asthma. Allergen-driven production of IL-4, IL-5 and IL-13 are typical of allergic pathologies and the secretion of such Th2-cytokines initiates isotype class-switching of B cells towards IgE, increased mucus production and recruitment of eosinophils to the airways. Since CD4$^+$Th2 cells represent a co-ordinating cell type in some allergies, it was suggested that the induction of counterbalancing responses might prevent the subsequent development of atopic disease. According to this modification of Strachan's hygiene hypothesis (Romagnani et al. Int Arch Allergy Immunol 1992; 98(4):279-85), microbial exposure may activate innate immune pathways that alter Th1, Th2 and Treg responses. This results in the suppression of T helper 2 cell expansion, and a consequent inhibition of isotype switching to IgE. However, several studies have suggested that viral and bacterial infections play a role in exacerbation of respiratory disease. For example, respiratory syncytial virus and Th1 inducing virulent *Bordetella pertussis* infection (Ennis et al. Clin Exp Allergy 2004; 34(9):1488-97) exacerbate allergic inflammation in animal models.

Gram-negative *B. pertussis* causes whooping cough, a severe respiratory disease responsible for significant infant morbidity and mortality worldwide. Although immunizations with either killed whole cell vaccines (Pw) or more recent acellular subunit vaccines (Pa) have had success, a re-emergence of the disease in young adults has been reported (Das P. Lancet Infect Dis 2002; 2(6):322). Typically, *B. pertussis* does not acutely affect this age group; however, infected adults can act as reservoirs, and increase the likelihood of infants contracting the disease prior to vaccination. Most current vaccination regimes require three doses, beginning at 2 months of age necessitating 6 months for optimal protection. Therefore, there is a need for vaccines that induce strong protection against *B. pertussis* in neonates.

Virulent *B. pertussis* infection exacerbates airway pathology in a murine model of allergen driven inflammation, despite the induction of Th1 immunity (Ennis et al. Clin Exp Allergy 2004; 34(9):1488-97). Th2 inducing Pa vaccines protect against *B. pertussis*-induced exacerbation of allergic asthma, but induce IL-13 both at a systemic and local level (Ennis et al. Clin Diagn Lab Immunol 2005; 12(3):409-17). In contrast, systemic immunization with Th1 inducing Pw inhibits allergic airway responsiveness (Mills et al. Dev Biol Stand. 1998; 95:31-41), suggesting that protection from allergen-driven pathology is not simply modulation of Th1/Th2 responses, but is associated with the degree of airway damage at the time of priming, such that allergen priming via the respiratory tract airways during breakdown of the airway epithelial mesenchymal unit may be a more significant factor than Th11/Th2/Treg polarization. Recently, a genetically-attenuated live vaccine against *B. pertussis*. BPZE1, has been developed as a candidate neonatal vaccine against whooping cough (Mielcarek et al. PLoS Pathog 2006; 2(7): e65). This live recombinant *B. pertussis* strain induces strong local and systemic immune responses upon intranasal delivery. Administration via the nasal route mimics natural infection and is expected to promote long-lasting immunity in children from 1 month of age (Mascart et al. J Immunology 2003; 170(1):1504-9). Three virulence factors have been targeted for attenuation; pertussis toxin, tracheal cytotoxin and dermonecrotic toxin. Using allelic exchange, genes encoding these toxins were deleted or replaced with genetically inactivated analogues in order to induce protection, without the severe pathology associated with wild-type infection. However, the influence of BPZE1 administration on third party allergen priming and allergen induced pathology is not known.

SUMMARY OF THE INVENTION

The present invention relates to a life attenuated *Bordetella pertussis* vaccine which is deficient for tracheal cytotoxin (TCT), pertussis toxin (PTX), and dermonecrotic toxin (DNT) for prophylaxis or treatment of an allergen-driven airway pathology.

The present invention relates to a method for prophylaxis or treatment of an allergen-driven airway pathology in a subject, comprising administering to said subject an effective amount of a life attenuated *Bordetella pertussis* vaccine, wherein said life attenuated *Bordetella pertussis* vaccine is deficient for tracheal cytotoxin (TCT), pertussis toxin (PTX), and dermonecrotic toxin (DNT).

The present invention also relates to the use of a life attenuated *Bordetella pertussis* vaccine, which is deficient for tracheal cytotoxin (TCT), pertussis toxin (PTX), and dermonecrotic toxin (DNT) in the manufacture of a medicament for prophylaxis or treatment of an allergen-driven airway pathology.

DETAILED DESCRIPTION OF THE INVENTION

Examples of allergen-driven airway pathology are allergic asthma, Hay fever, interstitial lung diseases including pulmonary fibrosis.

Interstitial lung diseases including pulmonary fibrosis, may be caused by occupational or environmental exposures. Without wishing to be bound by theory, a life attenuated *Bordetella pertussis* vaccine, which is deficient for TCT, PTX, and DNT would reduce airway damage and remodelling during a period of environmental exposure (to the agent triggering Interstitial lung diseases) and would also protect against virulent *B. pertussis* exacerbation of pulmonary fibrosis.

By "subject" it is meant a human. Typically the subject is a neonate, an infant or an adult.

Life attenuated *Bordetella pertussis* vaccines which are deficient for tracheal cytotoxin (TCT), pertussis toxin (PTX), and dermonecrotic toxin (DNT) have been described in WO2007/104451 and in Mielcarek et al. (PLoS Pathog 2006; 2(7):e65). Recent advances in the understanding of *B. pertussis* virulence at the molecular level have allowed to rationally design a strategy for attenuation by removing or altering genes that are involved in the pathogenesis of whooping cough. Three virulence factors were genetically targeted: tracheal cytotoxin (TCT), pertussis toxin (PTX), and dermonecrotic toxin (DNT).

TCT is responsible for the destruction of ciliated cells in the trachea of infected hosts and may thus be involved in the cough syndrome. TCT is a breakdown product of peptidoglycan in the cell wall of Gram-negative bacteria, which generally internalize it into the cytosol by the AmpG transporter protein to be re-utilized during cell wall biosynthesis. *B. pertussis* AmpG is inefficient in the internalization of peptidoglycan breakdown products. The *B. pertussis* ampG gene can be replaced by *E. coli* ampG. The resulting strain expressed less than 1% residual TCT activity. Any heterologous ampG gene from gram-negative bacteria that release very small amounts of peptidoglycan fragments into the medium, can be used in the present invention. Examples of suitable heterologous ampG gene include, but are not limited to ampG gene from *Escherichia coli, Salmonella, Enterobacteriaceae, Pseudomonas, Moraxella, Helicobacter, Stenotrophomonas, Legionella*.

PTX is a major virulence factor responsible for the systemic effects of *B. pertussis* infections and is composed of an enzymatically active moiety, called S1, and a moiety responsible for binding to target cell receptors. It is also one of the major protective antigens. The natural ptx genes can be replaced by a mutated version coding for an enzymatically inactive toxin. This can be achieved by replacing Arg-9 by Lys, and Glu-129 by Gly in S1, two key residues involved in substrate binding and catalysis, respectively. Allelic exchange can be used to first delete the ptx operon, and then to insert the mutated version. The presence of the relevant toxin in the *B. pertussis* culture supernatants can be detected by immunoblot analysis.

Other mutations can also be made such as those described in U.S. Pat. No. 6,713,072, as well as any known or other mutations able to reduce the toxin activity to undetectable levels. Allelic exchange can also be used to remove the dnt gene. Although the role of DNT in the virulence of *B. pertussis* is not certain, it has been identified as an important toxin in the closely related species *Bordetella bronchiseptica* and displays lethal activity upon injection of minute quantities.

In a preferred embodiment, the life attenuated *Bordetella pertussis* vaccine is the BPZE1 strain.

The BPZE1 strain has been deposited with the Collection Nationale de Cultures de Microorganismes (CNCM, Institut Pasteur, 25 rue du Docteur Roux. F-75724 Paris Cedex 15, FRANCE) on Mar. 9, 2006 under the number CNCM 1-3585.

Typically, life attenuated *Bordetella pertussis* vaccines of the invention may also carry heterologous antigens. The life attenuated *Bordetella pertussis* vaccines may be used as vector, to bear at least one further heterologous nucleic acid sequence encoding a protein of interest. Typically, the protein encoded by at least one further heterologous nucleic acid sequence is a protein for which the expression is desired in the respiratory tract. Typically, the protein of interest may be an antigen, such as a viral or a bacterial antigen, against which an immune response is desired. Examples of life attenuated *Bordetella pertussis* vaccines carrying heterologous antigens have been disclosed for example by Si Ying Ho et al. (Infection and Immunity, 2008, 76(1), 111-119).

Formulation of the vaccines of the present invention can be accomplished using art recognized methods. The amount of vaccines of the invention to be administered to a subject and the regime of administration can be determined in accordance with standard techniques well known to those of ordinary skill in the pharmaceutical and veterinary arts taking into consideration such factors as the adjuvant (if present), the age, sex, weight, species and condition of the particular subject and the route of administration. The administration of the vaccine is usually in a single dose. Alternatively, the administration of the vaccine of the invention is made a first time (initial vaccination), followed by at least one recall (subsequent administration), with the vaccine.

Typically the vaccines can be administered by nasal administration or by inhalation. This type of administration is low in costs and enables the colonization by the life attenuated *Bordetella pertussis* vaccine of the invention of the respiratory tract. Nasal administration may be accomplished with a life attenuated *Bordetella pertussis* vaccine under the form of liquid solution, suspension, emulsion. Solutions and suspensions are administered as drops. Solutions can also be administered as a fine mist from a nasal spray bottle or from a nasal inhaler. Gels are dispensed in small syringes containing the required dosage for one application Inhalation may be accomplished with a life attenuated *Bordetella pertussis* vaccine under the form of solutions, suspensions, and powders; these formulations are administered via an aerosol, droplets or a dry powder inhaler. The powders may be administered with insufflators or puffers.

In the following, the invention will be illustrated by means of the following example as well as the figures.

FIGURE LEGENDS

FIG. 1. Attenuated *B. pertussis* BPZE1 reduces the severity of airway pathology induced by sensitizing allergen. Representative morphological changes at 38 days in bronchiolar transverse sections of lungs from (A) Non-sensitized, (B) OVA-sensitized, (C) OVA-sensitized and infected with *B. pertussis*, (D) OVA-sensitized and immunized with BPZE1. Airway inflammation was detected using haematoxylin and eosin (H&E) staining of fixed lung sections. Original magnification A, C, E & G ×100. B, D, F& H ×400.

Figure 2:
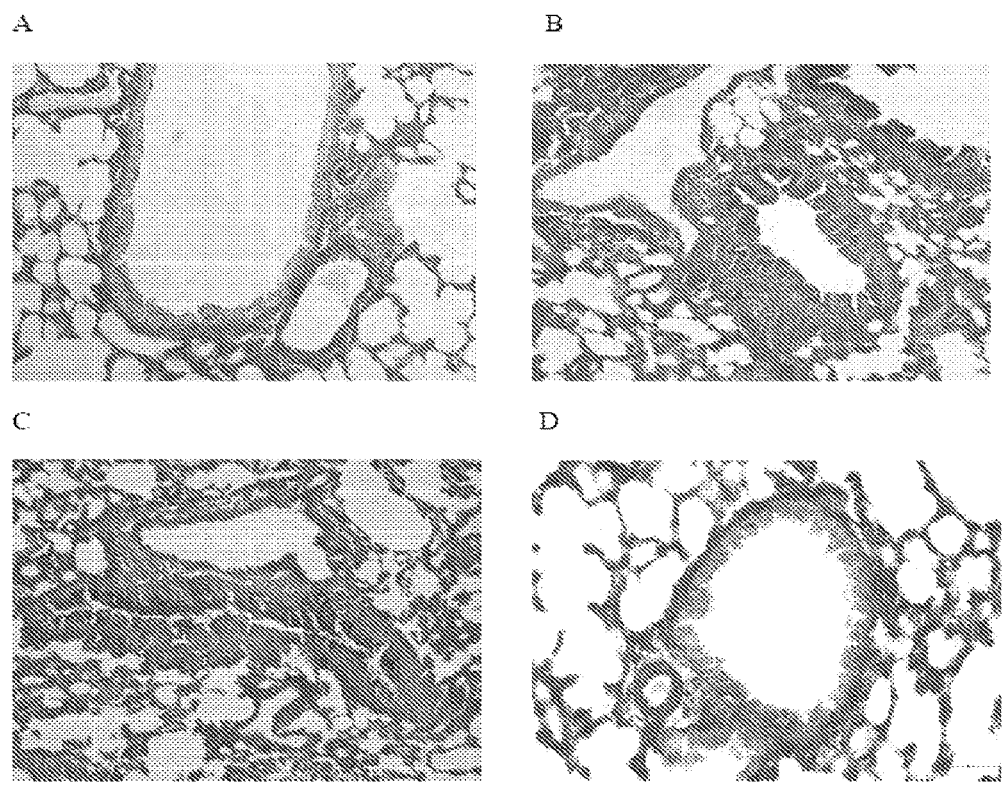

FIG. 2. Attenuated *B. pertussis* BPZE1 reduces the severity of mucus hyperplasia to sensitizing allergen. Representative morphological changes at 37 days in transverse sections of bronchioles from (A) non-sensitized, (B) OVA-sensitized, (C) OVA-sensitized and infected with *B. pertussis*, (D) OVA-sensitized and vaccinated with BPZE1. Airway inflammation was detected using combined Discombes/Alcian blue/PAS staining on lung sections. Original magnification ×400.

Figure 3:
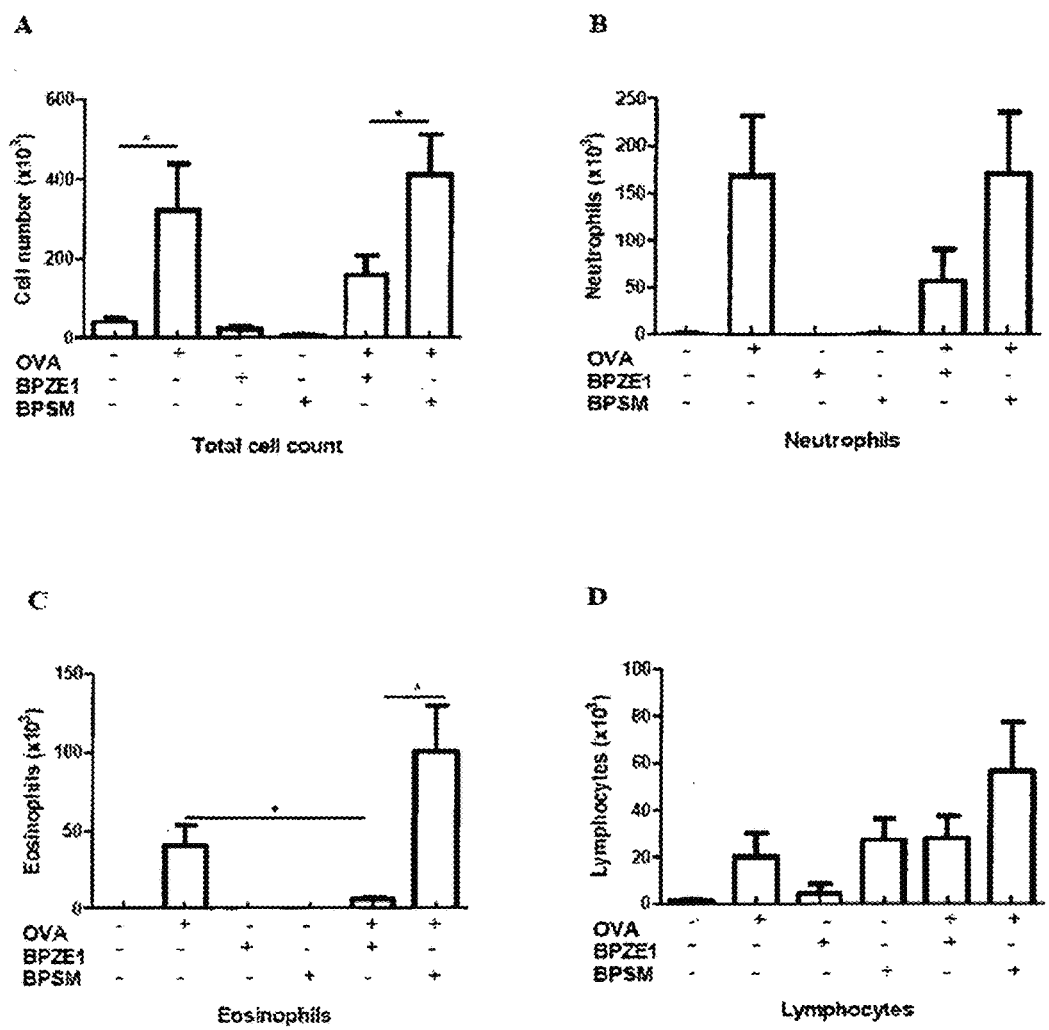

FIG. 3. Attenuated *B. pertussis* BPZE1 reduces the cell infiltrate of BAL fluid. Effect of virulent BPSM infection, attenuated BPZE1 challenge and/or OVA sensitization on BAL composition 24 h after final OVA exposure. Negative controls were sham infected/sensitized with saline. BAL fluid was examined for the total cell number (A), or the presence of neutrophils (B), eosinophils (C) or lymphocytes (D). Results are expressed as mean±S.E.M. of cell number. *$P<0.05$.

Figure 4:
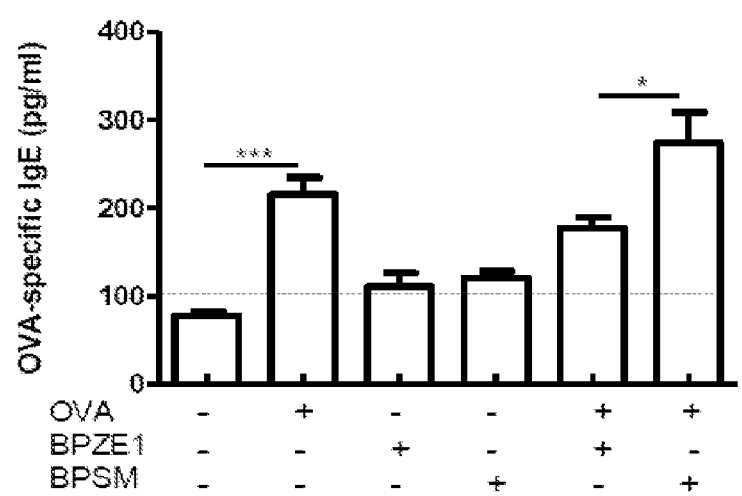

FIG. 4. Attenuated *B. pertussis* BPZE1 reduces allergen-induced IgE. OVA-specific IgE in serum elicited in response to OVA sensitization and/or challenge with virulent (BPSM) or attenuated (BPZE1) *B. pertussis*. Sera were collected on day 38 and OVA-specific serum IgE levels were measured by ELISA. Concentrations below 100 pg/ml were considered negative. Results are expressed as mean antibody concentrations ±S.E.M. $P<0.05$.

Figure 5:
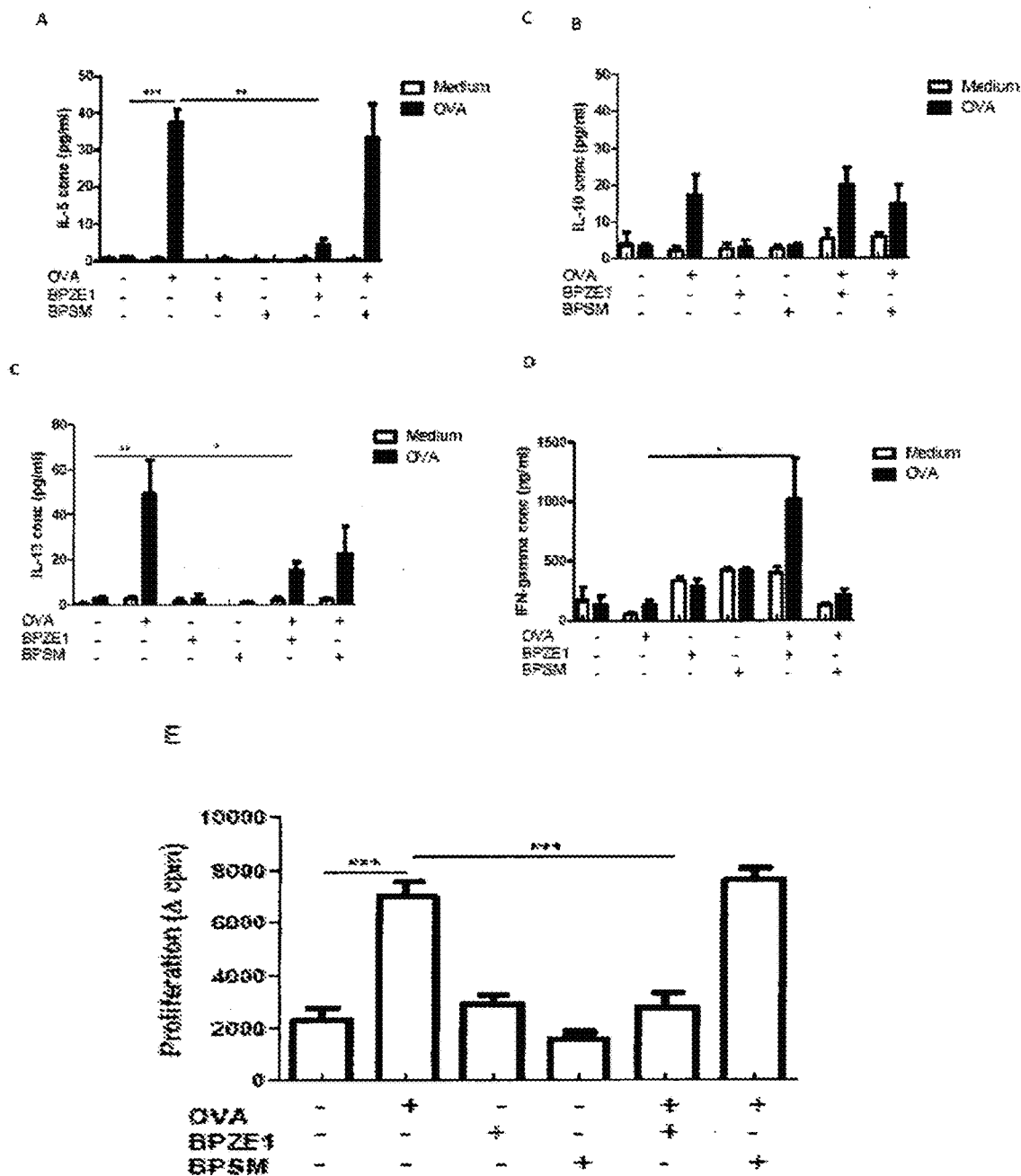

FIG. 5. Cell-mediated immune responses from splenocytes to OVA, elicited by OVA sensitization 10 days following prior exposure to attenuated (BPZE1) or virulent (BPSM) *B. pertussis* infection. Negative symbols indicate sham sensitization or challenge with PBS. Cytokine responses from similar cultures assayed are shown for (A) IL-5, (B) IL-10, (C) IL-13 and (D) IFN-γ. T-cell proliferation (E) represents Δcpm of spleen proliferation against OVA at 200 μg/ml following subtraction of background typically 2000-4000 cpm. Results are expressed as mean±S.E.M.

EXAMPLE

Abstract

This preclinical study examined whether the candidate *B. pertussis* vaccine BPZE1 influences third party allergen priming and pathology, using previously characterized animal models. Unlike virulent wildtype strains, live attenuated BPZE1 did not exacerbate but protected against allergen-driven pathology.

Abbreviations Used

OVA: Ovalbumin; BAL: Bronchoalveolar lavage; BPZE1: live attenuated *Bordetella pertussis*; Pa: Acellular pertussis vaccine; Pw: Whole-cell pertussis vaccine

Materials

Immunization, Sensitization and Airway Delivery of OVA and *B. pertussis*

Eight- to twelve-week old, female BALB/c mice (Harlan, Oxon, UK) were used and maintained according to the regulations and guidelines of the Irish Department of Health, and the Research Ethics Committee of the National University of Ireland, Maynooth. Mice were exposed to live virulent or attenuated bacteria, and sensitized to allergen during infection. Virulent *B. pertussis* BPSM or attenuated BPZE1 were cultured as previously described (Mills et al. Dev Biol Stand. 1998:95:31-41). Attenuated or virulent strains at mid-log growth were administered to mice by aerosol. At the peak of infection (10 d) and at 24 d, mice were sensitized by intra-peritoneal injection of 100 μg/ml ovalbumin (OVA) in adjuvant (AlumImject™, Pierce. Ill.). Mice were challenged intra-nasally with OVA (50 μg/ml) on days 24, 35, 36 and 37. Various control groups received sham delivery of sterile PBS in place of the active agent (Ennis et al. Clin Exp Allergy 2004; 34(9): 1488-97).

Bronchoalveolar Lavage (BAL) and Respiratory Tract Histology

On 37 d, mice were sacrificed by lethal injection of sodium pentobarbital and BAL fluid collected (Ennis et al. Clin Exp Allergy 2004:34(9):1488-97). Total leukocytes and differential cell counts were performed as described, using Diff Quik/Rapi-Diff II™ (Triangle Biomedical Sciences, NC, USA.). Lungs from non-lavaged mice were removed and fixed in 10% (v/v) formalin/PBS, embedded in paraffin, sectioned and stained with haemotoxylin/eosin (H&E), alcian blue (identification of mucus), Discombes (identification of eosinophils), or periodic acid-Schiff (for assessment of basement membrane thickness). Histopathological changes were graded according to an established semi-quantitative scoring system as mild, moderate or severe. Pathology was scored by two independent observers without prior knowledge of the treatment group as previously described (Ennis et al. Clin Diagn Lab Immunol 2005; 12(3):409-17).

T Cell Proliferation Assay

Splenocytes from mice were prepared as previously described (Mahon et al. J Exp Med 1997; 186(11):1843-1851) and incubated for 72 h with either medium (negative control), OVA (200 μg/ml), or concanavalin A (5 μg/ml). Supernatants were removed at 48 h for cytokine analysis,

TABLE I

Summary of pathological features of *B. pertussis*/allergen sensitization.

| Group | Tissue inflammation | BALF eosinophils | Goblet cell metaplasia | IL-5 | IL-13 | IL-10 | IFN-γ | OVA-IgE |
|---|---|---|---|---|---|---|---|---|
| Control | − | − | − | − | − | − | − | − |
| OVA | ++ | ++ | ++ | +++ | +++ | − | − | ++ |
| ZeOVA | + | + | + | − | + | − | ++ | + |
| SmOVA | ++ | +++ | +++ | + | − | − | − | +++ |
| BPZE1 | − | − | − | − | − | − | − | − |
| BPSM | − | − | − | − | − | − | − | − |

Features of airway inflammation in non-sensitized (Control), OVA-sensitized (OVA), BPZE1-immunized sensitized mice (ZeOVA) or BPSM-infected sensitized mice (SmOVA).

and cultures received fresh medium. Cells were incubated for the final 6 h with [$^3$H]-thymidine and proliferation was measured by radioactivity incorporated by liquid scintillation.

Measurement of Cytokines and Antibody Responses

Analysis of IL-5, IL-10, IL-13 and IFN-γ from BAL fluid and splenocyte supernatant was carried out using Cytometric Bead Array Flex Sets (BD Biosciences. Franklin Lakes, N.J.) according to manufacturer's instructions, and analysed by flow cytometry (Becton-Dickinson, New Jersey, USA). Standard curves and raw data were generated for each cytokine using FCAP Array v1.0.1 software (BD Biosciences). OVA-specific serum IgE was measured by ELISA as previously described (Morokata T et al. Immunology 1999: 98(3):345-351) using a rat anti-mouse IgE monoclonal antibody (BD Pharmingen, San Diego, Calif., USA). IgE concentration was expressed as μg/ml after comparison to murine IgE standards (BD, Pharmingen, San Diego, Calif., USA).

Statistical Analysis

Values for all measurements were expressed as the mean±standard error of the mean (SEM). Statistical analysis was performed using GraphPad Prism™ software (GraphPad, San Diego, Calif.). Comparison was made using the Kruskal Wallis test, or the Mann Whitney test as appropriate. Significance was denoted by P value<0.05.

Results

The Attenuated *B. pertussis* BPZE1 Prevents Exacerbated OVA-Driven Allergic Airway Pathology Virulent *B. pertussis* can exacerbate third party allergen priming in animal models (Ennis et al. Clin Exp Allergy 2004; 34(9): 1488-97) and has been associated with exacerbation of allergy in humans (Harju et al. Thorax 2006; 61(7):579-584). To assess the influence of attenuated *B. pertussis* on third party allergen priming, mice were primed with virulent or attenuated strains of *B. pertussis*, and sensitized to OVA at the peak of bacterial carriage (a model previously shown to uncover the influence of infection on allergen-driven inflammation). In the absence of infection, OVA sensitized mice exhibited typical peribronchial and perivascular inflammation at day 38, which was not observed in naïve control mice (FIGS. 1A and B). At this time point, pathology due to virulent bacterial infection alone has resolved. Priming at the peak of virulent *B. pertussis* infection enhanced airway pathology when compared to OVA sensitization alone, with mice displaying epithelial hyperplasia and moderate mucus metaplasia (FIG. IC). In contrast, minimal pathology was observed in sensitized mice infected with attenuated BPZE1, compared to those sensitized to OVA alone (FIG. 1D). An examination of mucus-containing goblet cells demonstrated that prior immunization with BPZE1 in OVA-sensitized mice reduced mucus secretion and hyperplasia, compared to those sensitized to OVA alone (FIG. 2). Thus unlike infection with virulent *B. pertussis*, immunization with the candidate live attenuated *B. pertussis* vaccine BPZE1 did not enhance, but reduced the pathology associated with allergen sensitization.

The Attenuated *B. pertussis* Vaccine Strain BPZE1 Prevents OVA-Driven Allergic Airway Inflammation Immunization with live attenuated *B. pertussis* BPZE1 moderated the quality of the OVA-induced inflammatory influx to the respiratory tract. Control mice showed minimal cellularity in bronchoalveolar lavage (FIG. 3), whereas OVA sensitization/challenge resulted in significant infiltration by inflammatory cells (>3×10$^6$ cells, FIG. 3A, p<0.05). There were few remarkable differences in the numbers of lymphocytes or neutrophils. BPZE1 immunization alone did not support a neutrophil infiltration at 38 d and infiltration of neutrophils in combined BPZE1/OVA sensitized mice was typically lower than either OVA alone or in combination with virulent bacteria, however this did not achieve statistical significance in this study. The key observations were that prior infection with virulent *B. pertussis* increased cellular infiltration compared to sensitization by OVA alone accompanied by increased eosinophilia (FIG. 3C) as previously observed (Ennis et al. Clin Exp Allergy 2004; 34(9): 1488-97). However in marked contrast immunization with live attenuated BPZE1 prior to OVA sensitization resulted in significantly reduced OVA driven eosinophil infiltration of the airways (FIG. 3C, p<0.05). Thus, the candidate live attenuated *B. pertussis* vaccine BPZE1 prevents OVA-driven allergic airway eosinophilia—a key feature of inflammation in this model.

The Candidate Live *B. pertussis* Vaccine BPZE1 does not Enhance Serum IgE Responses to Sensitizing Allergen OVA sensitization in mice is known to induce IgE and a powerful specific Th2 response, whereas *B. pertussis* infection induces a strong Th1 response. However, pertussis toxin alone can elevate IgE concentrations. Therefore, it was important to explore whether attenuated BPZE1 had an adjuvant effect or enhanced allergen-specific IgE. The influence of BPZE1 on allergic sensitization was examined by measuring the concentration of OVA-specific IgE in serum from mice sensitized to OVA, infected with BPSM, immunized with BPZE1, or receiving combinations of these treatments (FIG. 4). OVA sensitization induced significant levels of IgE as is well documented. Previously, a significant increase in OVA-specific IgE following infection with virulent *B. pertussis* W28 was observed in OVA-sensitized mice (Ennis et al. Clin Exp Allergy 2004; 34(9):1488-97). IgE responses in mice exposed to attenuated BPZE1 prior to OVA sensitization did not differ significantly to those receiving OVA alone. However, in marked contrast, attenuated BPZE1 immunization resulted in significantly reduced induction (p<0.05) of OVA-induced IgE compared to mice infected with virulent BPSM in combination with OVA sensitization (FIG. 4). Therefore, the candidate live attenuated *B. pertussis* vaccine BPZE1 delivered prior to allergen priming demonstrated no enhanced IgE response as observed with *B. pertussis* W28[11] and BPSM.

The Live Attenuated *B. pertussis* Vaccine BPZE1 Modulates Recall Cytokine Responses to Sensitizing Allergen It is clear that attenuated BPZE1 has a radically different effect on allergen-driven airway pathology compared to virulent *B. pertussis*. In order to uncover the mechanistic basis of this effect, the influence of bacterial exposure on the pattern of allergen-induced immune responses was characterized. Allergen-specific cytokine induction by spleen cell preparations was assessed following immunization with BPZE1 and OVA sensitization/challenge in order to evaluate the influence of BPZE1 on allergen-induced priming. As expected, OVA sensitization alone induced high levels of the Th2 cytokines IL-S and IL-13 (FIG. 5) on recall to OVA. Neither virulent BPSM nor attenuated BPZE1 alone induced any recall response to OVA (FIG. 5E), but did produce strong Th1 responses to *B. pertussis* antigens. BPSM challenge did not modulate the immune response to sensitizing allergen, with no significant reduction in OVA specific IL-5, IL-13 or proliferative responses observed in mice co-sensitized to OVA, and no significant increase in IFN-γ(FIG. 5). In contrast, attenuated BPZE1 altered the pattern of cytokines induced by sensitizing allergen. BPZE1 significantly reduced the levels of OVA-induced IL-5 ($p<0.005$) and IL-13 ($p<0.05$), as well as OVA specific proliferative responses ($p<0.001$), but induced significantly increased IFN-γ in response to OVA ($p<0.05$). In summary, BPZE1 did not promote Th2 cytokine induction to third party antigen but rather modulated this to a Th1 like response.

DISCUSSION

The present study used combined infection/sensitization models to demonstrate that an attenuated strain of *B. pertussis*, BPZE1, did not enhance but reduced allergen-driven airway pathology. Attenuated *B. pertussis* reduced allergen-driven lung eosinophilia and decreased the severity of airway inflammation. Furthermore, BPZE1 prevented an increase in OVA-induced IL-5 and IL-13 and modulated recall responses to allergen to a Th1 like response. BPZE1 demonstrated reduced allergen-induced serum IgE responses when compared to mice infected with virulent *B. pertussis* prior to OVA sensitization (see Table I). Taken together these data demonstrate that attenuated BPZE1 does not exacerbate allergen-induced airway pathology in a murine model and supports the use of this candidate vaccine for populations where atopy is prevalent.

The hygiene hypothesis suggests that Th1-inducing infections may have an inhibitory effect on the development of atopy. However, previous studies have demonstrated that virulent *B. pertussis* enhances the severity of airway pathology (Ennis et al. Clin Exp Allergy 2004; 34(9): 1488-97) despite induction of Th1 immunity. In contrast, systemic immunization with a Th1-inducing Pw vaccine inhibited allergic airway responsiveness, suggesting that protection from allergen-driven pathology is linked not just to CD4+ T cell profile, but also to the degree of airway damage at the time of priming.

The purpose of this study was to investigate whether immunization with a genetically attenuated strain of *B. pertussis* could protect against OVA-induced airway inflammation. Previously, the potential of other vaccines to moderate the risk of atopy has been investigated and a number of studies have found an inverse relationship between immunization and an increased risk of allergic disease. Ennis et at found that a Pw vaccine protected against *B. pertussis*-exacerbation of OVA-induced airway hyperresponsiveness in a murine model of allergic airway inflammation (Mills et al. Dev Biol Stand. 1998; 95:31-41). Likewise, Grüber et at found no allergy-promoting effect in response to common childhood vaccines including pertussis vaccines (Grüber et al. Allergy 2008; 63(11): 1464-72). The relationship between childhood immunization and the development of atopic diseases in a population-based sample of 718 adolescents found that live attenuated vaccines inhibited the development of asthma and allergic diseases (Martignon et al. Pediatr Allergy Immunol. 2005; 16(3):193-200). The current study demonstrates that the vaccine candidate BPZE1 suppresses allergen-driven pathology through a mechanism that modulates cell-mediated responses against OVA at both a mucosal and systemic level.

IL-5-mediated recruitment of eosinophils to the lung contributes to allergen-induced airway pathology by generating potent cytotoxic products, including major basic protein (MBP) and eosinophil peroxidase, which collectively contribute to tissue damage (Gleich G. J Allergy Clin Immunol 2000; 105(4):651-63). Infection with virulent *B. pertussis* exacerbates the extent of the OVA-induced inflammatory influx to the respiratory tract, with an increase in eosinophils (FIG. 3C), accompanied by a marked increase in the severity of airway pathology (FIG. 1G). Conversely, administration of attenuated BPZE1 prior to allergen sensitization resulted in a significant reduction in eosinophil infiltration. This study demonstrates that BPZE1 prevents the adjuvant-associated increase in OVA-induced IL-5 (FIG. 1A) seen when animals are infected with virulent *B. pertussis* strains. 11-13 also contributes to the pathogenesis of asthma by promoting Th2 responses, increasing eosinophil recruitment, and contributing to IgE-mediated inflammation (Humbert et al. J Allergy Clin Immunol. 1997:99(5):657-65; Temann et al. Am J Respir Cell Mol Biol 1997; 16(4):471-8). Attenuated BPZE1 significantly decreased OVA induced IL-13 in sensitized mice (FIG. 5C). Airway mucus hypersecretion is also linked to IL-13 and is a major pathophysiological feature of both allergic asthma and whooping cough. It is not surprising therefore that mucus production mirrored IL-13 levels in this study and was significantly reduced in sensitized mice previously exposed to BPZE1 (FIG. 5C).

This study suggests that one, or a combination, of the attenuated virulence factors in BPZE1 (pertussis toxin, tracheal cytotoxin and dermonecrotic toxin) play a role in the adjuvant effect observed with virulent *B. pertussis* strains, via the induction of either IL-5 or IL-13, or both. The protection against allergen-driven pathology seen here is associated with three genetic modifications contained within BPZE1 and modulation of the allergic immune response is consistent with some versions of the hygiene hypothesis. However, the mechanisms underlying the beneficial influence of attenuated BPZE1 on allergen-driven pathology may be multiple and inter-linked. Previous studies have demonstrated a significant increase in total serum IgE as a result of OVA sensitization in animal models (Holgate et al. J Allergy Clin Immunol 2005; 115(3):459-465; Hamelmann et al. Allergy 1999:54(4):297-305). Here, allergen-specific IgE responses induced by respiratory sensitization were significantly reduced in mice receiving attenuated compared to virulent *B. pertussis*. This is consistent with the modulation of systemic immune responses to OVA induced by attenuated BPZE1 away from IL-5 and IL-13 towards IFN-γ, a response which is associated with reduced IgE (Lack et al. J Immunol 1994:152(5):2546-54). Nevertheless allergic airway inflammation is not simply a balance between Th1 and Th2 responses. Hansen et at have shown that modulation of airway CD4' Th responses does not necessarily reduce airway pathology (Hansen et al. J Clin Invest 1999; 103(2): 175-183). It might be that the key beneficial feature of BPZE1 is the combination of a Th1 skewed response combined with the absence of induced airway pathology. This is consistent with previous reports in which exacerbation of airway pathology to allergen was associated with allergen priming during a period of airway damage or remodelling (Marsland et al. Clin Exp Allergy 2004; 34(8):1299-306; Gem. J Allergy Clin Immunol 2000:105(2 Pt 2):S497-502). This combined benefit makes life attenuated *Bordetella pertussis* vaccine which is deficient for TCT, PTX, and DNT an attractive candidate as a protective agent against atopy.

REFERENCES

Throughout this application, various references describe the state of the art to which this invention pertains. The disclosures of these references are hereby incorporated by reference into the present disclosure.

What is claimed is:

1. A method for preventing or reducing chronic airway inflammation induced in response to exposure to an allergen which induces a Th2 response in a subject, the method comprising the step of infecting the subject's respiratory tract with a live *Bordetella pertussis* strain which is deficient for tracheal cytotoxin (TCT), pertussis toxin (PTX), and dermonecrotic toxin (DNT), wherein the step of infecting the subject's respiratory tract results in the subject developing a Th1 immune response which prevents or reduces the development of chronic airway inflammation induced in response to exposure to the allergen.

2. The method of claim 1, wherein the strain comprises a mutated pertussis toxin (ptx) gene, a deleted or mutated dermonecrotic (dnt) gene, and a heterologous ampG gene.

3. The method of claim 2, wherein the heterologous ampG gene is an *E. coli* ampG gene that replaces the wild-type *Bordetella* strain ampG gene.

4. The method of claim 2, wherein the mutation of the ptx gene comprises the substitution of an amino acid involved in substrate binding and/or an amino acid involved in catalysis.

5. The method of claim 4, wherein the substitution of the amino acid involved in substrate binding comprises R9K and the substitution of the amino acid involved in catalysis comprises E129G.

6. The method of claim 2, wherein the heterologous ampG gene is the only heterologous gene in the strain.

* * * * *